(12) United States Patent
Tanaka

(10) Patent No.: US 9,421,186 B2
(45) Date of Patent: Aug. 23, 2016

(54) METHOD FOR IMPROVING THERAPY FOR AUTOIMMUNE DISEASES SUCH AS RHEUMATOID ARTHRITIS

(75) Inventor: Keiichi Tanaka, Toyama (JP)

(73) Assignee: TOYAMA CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/241,655

(22) PCT Filed: Aug. 29, 2012

(86) PCT No.: PCT/JP2012/071840
§ 371 (c)(1),
(2), (4) Date: Feb. 27, 2014

(87) PCT Pub. No.: WO2013/031831
PCT Pub. Date: Mar. 7, 2013

(65) Prior Publication Data
US 2015/0080356 A1    Mar. 19, 2015

(51) Int. Cl.
| | |
|---|---|
| A01N 45/00 | (2006.01) |
| A61K 31/56 | (2006.01) |
| A01N 43/58 | (2006.01) |
| A01N 43/60 | (2006.01) |
| A61K 31/50 | (2006.01) |
| A61K 31/495 | (2006.01) |
| A61K 31/352 | (2006.01) |
| C07D 311/22 | (2006.01) |
| A61K 45/06 | (2006.01) |
| A61K 31/519 | (2006.01) |
| A61K 31/573 | (2006.01) |
| A61K 9/20 | (2006.01) |

(52) U.S. Cl.
CPC ............ *A61K 31/352* (2013.01); *A61K 9/2054* (2013.01); *A61K 31/519* (2013.01); *A61K 31/573* (2013.01); *A61K 45/06* (2013.01); *C07D 311/22* (2013.01)

(58) Field of Classification Search
None
See application file for complete search history.

(56) References Cited

U.S. PATENT DOCUMENTS

| | | | |
|---|---|---|---|
| 5,922,755 A | 7/1999 | Tanaka et al. | |
| 6,166,068 A | 12/2000 | Tanaka et al. | |
| 8,865,728 B2 * | 10/2014 | Godessart Marina et al. | 514/262.1 |
| 2009/0035315 A1 * | 2/2009 | Christgau et al. | 424/145.1 |
| 2010/0158905 A1 | 6/2010 | Pearlman et al. | |

FOREIGN PATENT DOCUMENTS

| | | |
|---|---|---|
| EP | 2 210 615 A1 | 7/2010 |
| JP | 3521145 | 2/2004 |
| WO | WO 2007/042035 A2 | 4/2007 |

OTHER PUBLICATIONS

Du et al., "T-614, a novel immunomodulator, attenuates joint inflammation and articular damage in collagen-induced arthritis," Arthritis Research and Therapy, 2008, 10:R136 Published Nov. 19, 2008.*
U.S. Appl. No. 14/647,931, filed May 28, 2015, Tanaka, et al.
Du, Fang., et al., "T-164, a novel immunomodulation, attenuates joint inflammation and articular damage in collagen-induced arthritis", Arthritis Research & Therapy, vol. 10, No. 6, R136, (2008).
Urata, N., Et al., "Effect of Disease-modifying Antirheumatic Drug Iguratimod (T-614) on Chronic Arthritis in Experimental Animals", Japan Pharmacology Ther. (Basic Pharmacology & Therapeutics), vol. 35, No. 6 , pp. 571-578, (2007).
"Arthritis & Rheumatism" , Guidelines for the Management of Rheumatoid Arthritis, American College of Rheumatology, vol. 39, No. 5 , pp. 713-722,( May 1996).
"Arthritis & Rheumatism" Guidelines for the Management of Rheumatoid Arthritis, American College of Rheumatology, vol. 46. No. 2, pp. 328-346, (Feb. 2002).
Inaba, T., "Synthesis and Antiinflammatory Activity of 7-Methanesulfonylamino-6-phenoxychromones. Antiarthritic Effect of the 3-Formylamino Compound (T-614) in Chronic Inflammatory Disease Models", Chem. Pharm. Bull., vol. 48, pp. 131-139, (2000).
Tanaka, K., et al., "Pharmacological Studies on 3-Formylamino 7-methylsulfonylamino-6-phenoxy-4H-1-benzopyran-4-one (T-614), a Novel Antiinflammatory Agent. $4^{th}$ Communication: Inhibitory Effect on the Production of Interleukin-1 and Inteleukin-6", J. Pharmacobio-Dyn., vol. 15, pp. 649-655, (1992).
Tanaka, K., "Pharmacological Studies on T-614, A Novel Antiinflammatory Agent:: Effect on type II Collagen-induced Arthritis in DBA/1J Mice and Spontaneous Arthritis in MRL/1 Mice", Int. J. Immunotherapy IX(2), vol. 9 , pp. 69-78, (1993).
Hara, M., et al., "Efficacy and safety of iguratimod compared with placebo and salazosulfapyridine in active rheumatoid arthritis: a controlled, multicenter, double-blind, parallel-group study", Mod Rheumatol, vol. 17, pp. 1-9, (2007).
O'Dell, R. J., "Treatment of Rheumatoid Arthritis with Methotrexate Alone, Sulfasalazine and Hydroxychloroquine, of a Combination of all Three Medications", Treatment of Riieumatoid Artiiritis, vol. 334, No. 20, pp. 1287-1291, (1996).

(Continued)

*Primary Examiner* — Jared D Barsky
(74) *Attorney, Agent, or Firm* — Oblon, McClelland, Maier & Neustadt, L.L.P

(57) ABSTRACT

In the present invention, a method using a combination of iguratimod or a salt thereof and one or more immunosuppressants is useful as a method for the treatment of autoimmune diseases, and with this method adverse effects are lessened. A pharmaceutical composition containing this combination is useful for the treatment of autoimmune diseases. This method and pharmaceutical composition are useful for the treatment of more severe autoimmune diseases.

2 Claims, No Drawings

(56) References Cited

OTHER PUBLICATIONS

International Search Report Issued Oct. 2, 2012 in PCT/JP12/071840 Filed Aug. 29, 2012.
Office Communication and Partial Supplementary European Search Report issued on Feb. 3, 2015 in Application No. 12827070.9.
M. Hara, et al., "Efficacy and safety evaluation of iguratimod, a novel anti-rheumatic agent—a double-blind, comparative study of iguratimod-MTX combination in rheumatoid arthritis patients with an inadequate response to MTX", Annals of the reheumatic diseases, vol. 71, No. Suppl. 3, XP008174469, Jun. 2012, pp. 124-125.
Manfred Lehmann, et al., "Fumaric acid esters are potent immunosuppressants: inhibition of acute and chronic rejection in rat kidney transplantation models by methyl hydrogen fumarate", Archives of Dermatological Research, XP 055164425, Dec. 1, 2002, pp. 399-404.
Yutaka Kawano, et al., "Cell action mechanism of tranilast—Effect on the expression of HLA-class II antigen", International Journal of Immunopharmacology, vol. 15, No. 4, XP023811849, May 1, 1993, pp. 487-500.
Masako Hara, et al., "Safety and efficacy of combination therapy of iguratimod with methotrexate for patients with active rheumatoid arthritis with an inadequate response to methotrexate: an open-label extension of a randomized, double-blind placebo-controlled trial", Modern Rheumatology/The Japan Rheumatism Association May 2014, vol. 24, No. 3, XP008174468, May 2014, pp. 410-418.
H. A. M. Mucke, "Iguratimod: A New Disease-Modifying Antirheumatic Drug", Drugs of Today, vol. 48, No. 9, XP008174465, Sep. 2012, pp. 577-586.

* cited by examiner

METHOD FOR IMPROVING THERAPY FOR AUTOIMMUNE DISEASES SUCH AS RHEUMATOID ARTHRITIS

CROSS REFERENCE TO RELATED APPLICATIONS

The present application is a 35 U.S.C. §371 national stage patent application of International patent application PCT/JP2012/071840, filed on Aug. 29, 2012, published as WO/2013/031831 on Mar. 7, 2013, the text of which is incorporated by reference, and claims the benefit of the filing date of Japanese application no. 2011-188011, filed on Aug. 30, 2011, the text of which is also incorporated by reference.

BACKGROUND OF THE INVENTION (1) Field of the Invention

The present invention relates to a method of using iguratimod (N-[7-[(methanesulfonyl)amino]-4-oxo-6-phenoxy-4H-1-benzopyran-3-yl]formamide) or a salt thereof and an immunosuppressive agent in combination for the treatment such as the therapy or prevention of autoimmune diseases. The present invention also relates to a pharmaceutical composition containing iguratimod or a salt thereof and an immunosuppressive agent, which is useful in the treatment such as therapy or prevention of autoimmune diseases.

(2) Description of Related Art

Chronic arthritis caused by connective tissue diseases typified by autoimmune diseases such as rheumatoid arthritis brings about, for example, dysfunction due to the progression of cartilage and/or bone destruction, and largely affects daily life. Although the cause of such autoimmune diseases remains unclear, these diseases are considered to be triggered by excessive immune response to autoantigens.

Against this backdrop, disease-modifying anti-rheumatoid drugs (DMARDs) typified by immunomodulatory drugs (e.g., gold preparation, D-penicillamine, and salazosulfapyridine) and immunosuppressive agents (e.g., methotrexate and tacrolimus) are used as the first drug of choice in the medical therapy of rheumatoid arthritis and other types of arthritis or autoimmune diseases. Particularly, for the therapy of rheumatoid arthritis, use of DMARDs from an early stage after definitive diagnosis is recommended by treatment guidelines (Arthritis Rheum. Vol. 39, p. 713-722 (1996); and Arthritis Rheum. Vol. 46, p. 328-346 (2002)). Now, immunological therapy is absolutely important for this disease. In addition, steroidal anti-inflammatory drugs and nonsteroidal anti-inflammatory drugs (NSAIDs) such as aspirin or indomethacin are used according to the symptoms of patients. These therapeutic methods currently used, however, cannot completely suppress the progression of joint or bone destruction, which is the biggest problem in arthritis, and long-term use thereof is difficult in terms of adverse reactions. Thus, these therapeutic methods have not yet provided as a satisfactory treatment.

Immunosuppressive agents are known to be effective for autoimmune diseases. These immunosuppressive agents inhibit antibody production, cytokine production, and lymphocyte or synovial cell proliferation, etc., thereby suppressing excessive autoimmune phenomena and, by extension, symptoms of arthritis or the like. Methotrexate, leflunomide, and tacrolimus are commercially available as immunosuppressive agents. Drug development is still continuing. Moreover, steroid drugs have strong immunosuppressive effects, as well known.

Iguratimod having anti-arthritic effects exhibits inhibitory effects on cytokine production and immunomodulatory effects (Chem. Pharm. Bull., Vol. 48, p. 131-139 (2000); J. Pharmacobio-Dyn., Vol. 15, p. 649-655 (1992); and Int. J. Immunotherapy, Vol. 9, p. 69-78 (1993)) and is useful in the therapy of rheumatoid arthritis and other types of arthritis or autoimmune diseases (Japanese Patent No. 3521145). Unfortunately, iguratimod is known to have adverse reactions such as hepatocellular damage (Mod. Rheumatol., Vol. 17, p. 1-9 (2007)).

A method using therapeutic drugs for arthritis in combination is known (N. Engl. J. Med., Vol. 334, p. 1287-1291 (1996)) and, however, does not produce satisfactory therapeutic effects due to the limited number of therapeutic drugs for arthritis. Also, such combined use is generally known to produce the additional or additive effect of improving arthritis symptoms. Reportedly, the combined use of iguratimod and methotrexate potentiates therapeutic effects on arthritis (Arthritis Research & Therapy), Vol. 10, No. 6, R136 (2008)).

However, it has been totally unknown so far that the combined use of therapeutic drugs for arthritis reduces the respective adverse reactions of the drugs.

BRIEF SUMMARY OF THE INVENTION

There is a demand for a method and a pharmaceutical composition which have a reduced adverse reaction and which are useful in the treatment such as therapy or prevention of autoimmune diseases.

Under such circumstances, the present inventor has conducted diligent studies and consequently completed the present invention by finding that a method using iguratimod or a salt thereof and one or more immunosuppressive agents in combination reduces an adverse reaction of the immunosuppressive agent, further potentiates therapeutic effects on autoimmune diseases, and is useful as a method for treatment such as therapy or prevention of autoimmune diseases.

Specifically, the present inventor has found the following aspects [1] to [11] and completed the present invention:

[1] A pharmaceutical composition for treatment of autoimmune diseases, comprising iguratimod or a salt thereof and one or more immunosuppressive agents.

[2] Medicament for treatment of autoimmune diseases, comprising a combination of iguratimod or a salt thereof and one or more immunosuppressive agents.

[3] A method for treating autoimmune diseases, comprising using iguratimod or a salt thereof and one or more immunosuppressive agents in combination to reduce an adverse reaction.

[4] A method for treating autoimmune diseases, comprising simultaneously or separately administering effective amounts of a preparation comprising iguratimod or a salt thereof as an active ingredient and a preparation comprising one immunosuppressive agents as an active ingredient to a patient.

[5] An agent for reducing an adverse reaction derived from therapy of autoimmune diseases, comprising iguratimod or a salt thereof and one or more immunosuppressive agents.

[6] An agent for reducing an adverse reaction of immunosuppressive agents, comprising iguratimod or a salt thereof.

[7] A treatment method for reducing an adverse reaction of immunosuppressive agents, comprising using a combination of iguratimod or a salt thereof and one or more immunosuppressive agents.

[8] A method for reducing an adverse reaction of immunosuppressive agents, comprising simultaneously or separately administering effective amounts of a preparation comprising iguratimod or a salt thereof as an active ingredient and a preparation comprising one or more immunosuppressive agents as an active ingredient to a patient.

[9] A method for treating autoimmune diseases, comprising administering one or more immunosuppressive agents and administering, simultaneously therewith or separately therefrom, iguratimod or a salt thereof to reduce an adverse reaction of the immunosuppressive agent.

[10] Use of iguratimod or a salt thereof and one or more immunosuppressive agents in combination to produce a medicament for treatment of autoimmune diseases.

[11] A kit for treatment of autoimmune diseases, comprising a preparation comprising iguratimod or a salt thereof as an active ingredient and a preparation comprising one or more immunosuppressive agents as an active ingredient.

The method using iguratimod or a salt thereof and one or more immunosuppressive agents in combination is useful as a method for treating autoimmune diseases with a reduced adverse reaction. A pharmaceutical composition containing these ingredients is useful in the treatment of autoimmune diseases.

The method and the pharmaceutical composition of the present invention are useful in the treatment of more severe autoimmune diseases.

DETAILED DESCRIPTION OF THE INVENTION

Hereinafter, the present invention will be described in detail.

Iguratimod is produced by the combination of methods known per se in the art and can be produced, for example, by the method described in Chem. Pharm. Bull., Vol. 48, p. 131-139 (2000).

Examples of the salt of iguratimod include: salts with alkali metals such as sodium and potassium; salts with alkaline earth metals such as calcium and magnesium; ammonium salt; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine.

Among the salts, preferable examples of the salt include pharmacologically acceptable salts.

Examples of the autoimmune diseases according to the present invention include:

arthritic diseases such as rheumatoid arthritis, juvenile idiopathic arthritis, and psoriatic arthritis; inflammatory bowel diseases such as ulcerative colitis and Crohn's disease; systemic lupus erythematosus; scleroderma; Behcet's disease; multiple sclerosis; rheumatic fever; polymyositis; periarteritis nodosa; Sjogren's syndrome; active chronic hepatitis; and glomerulonephritis. Preferable examples thereof include arthritic diseases, with rheumatoid arthritis more preferred.

Examples of the immunosuppressive agent used in the present invention include, for example, nucleic acid synthesis inhibitors such as methotrexate, azathioprine, and mizoribine; immunosuppressive agents such as leflunomide and tacrolimus; and compounds having immunosuppressive effects such as steroidal anti-inflammatory drugs such as dexamethasone, prednisolone, and cortisone acetate. Preferable examples thereof include nucleic acid synthesis inhibitors and steroidal anti-inflammatory drugs. More preferable examples thereof include methotrexate and prednisolone, with methotrexate further preferred.

The method of the present invention using iguratimod or a salt thereof and one or more immunosuppressive agents in combination is useful as a method for treating autoimmune diseases.

The method of the present invention using iguratimod or a salt thereof and one or more immunosuppressive agents in combination can reduce an adverse reaction and is useful in the treatment of autoimmune diseases.

The pharmaceutical composition of the present invention comprising iguratimod or a salt thereof and one or more immunosuppressive agents is useful in the treatment of autoimmune diseases.

Examples of the treatment of autoimmune diseases according to the present invention include the therapy or prevention of autoimmune diseases. More preferably, the method and the pharmaceutical composition of the present invention are used in the therapy of autoimmune diseases.

The method and the pharmaceutical composition of the present invention are capable of treating more severe autoimmune diseases. Also, the individual drugs used, even when administered in reduced amounts, exhibit strong effects. Thus, the adverse reaction of each drug can be reduced.

The pharmaceutical composition of the present invention comprising iguratimod or a salt thereof and one or more immunosuppressive agents can reduce an adverse reaction and is useful in the treatment of autoimmune diseases.

Also, the medicament of the present invention can reduce an adverse reaction and is useful in the treatment of autoimmune diseases.

The agent reducing an adverse reaction, comprising iguratimod or a salt thereof and one or more immunosuppressive agents is useful as an agent reducing an adverse reaction derived from therapy of autoimmune diseases.

This iguratimod or the salt thereof is useful as an agent reducing an adverse reaction of an immunosuppressive agent.

Examples of the adverse reaction reduced by the present invention include adverse reactions attributed to the one or more immunosuppressive agents and/or iguratimod. The present invention is further useful in reducing an adverse reaction attributed to the one or more immunosuppressive agents.

Specific examples of the adverse reaction reduced by the present invention include bone-marrow toxicity (reticulocytopenia), involution of lymphoid organs, and hepatocellular damage. The present invention is further useful in reducing bone-marrow toxicity or hepatocellular damage.

Examples of the adverse reaction of one or more immunosuppressive agents reduced by the present invention include bone-marrow toxicity (reticulocytopenia), involution of lymphoid organs, and hepatocellular damage. The present invention is further useful in reducing bone-marrow toxicity or hepatocellular damage.

Examples of the adverse reaction of iguratimod reduced by the present invention include hepatocellular damage.

These adverse reactions can be assayed, for example, by the blood biochemical tests with respect to aspartate aminotransferase (AST), alanine aminotransferase (ALT), and/or lactate dehydrogenase (LDH).

In the present invention, the preparation comprising iguratimod or a salt thereof as an active ingredient and the preparation comprising one or more immunosuppressive agents as an active ingredient can be administered simultaneously or separately to a patient. Preferably, these preparations are simultaneously administered through an oral route.

The pharmaceutical composition, the medicament, the preparation, the kit, or the method of the present invention can be administered or applied to a patient that does not respond to one or more immunosuppressive agents.

The pharmaceutical composition, the medicament, the preparation, the kit, or the method of the present invention can further be administered or applied to a patient having an adverse reaction attributed to the one or more immunosuppressive agents.

The pharmaceutical composition, the medicament, or the preparation of the present invention may contain one or more pharmaceutically acceptable additives and may be mixed appropriately with, for example, an excipient, a diluent, and a base usually used in formulation.

Examples of the excipient include: sugar alcohols such as erythritol, mannitol, xylitol, and sorbitol; sugars such as saccharose, powder sugar, lactose, and glucose; cyclodextrins such as α-cyclodextrin, β-cyclodextrin, γ-cyclodextrin, hydroxypropyl β-cyclodextrin, and sodium sulfobutylether β-cyclodextrin; celluloses such as crystalline cellulose and microcrystalline cellulose; and starches such as corn starch, potato starch, and pregelatinized starch.

Examples of the diluent include water, ethyl alcohol, Macrogol, propylene glycol, citric acid, acetic acid, phosphoric acid, lactic acid, sodium lactate, sulfuric acid, and sodium hydroxide.

Examples of the base include white petrolatum, polyethylene, paraffin, glycerin, cellulose derivatives, polyethylene glycol, silicon, and bentonite.

Examples of other additives include: disintegrants such as carmellose, carmellose calcium, croscarmellose sodium, sodium carboxymethyl starch, crospovidone, low-substituted hydroxypropylcellulose, and partially pregelatinized starch; binders such as hydroxypropylcellulose, carmellose sodium, and methylcellulose; lubricants such as stearic acid, magnesium stearate, calcium stearate, talc, hydrated silicon dioxide, light anhydrous silicic acid, and sucrose fatty acid ester; corrigents such as aspartame, saccharin, stevia, thaumatin, and acesulfame potassium; coloring agents such as titanium dioxide, iron sesquioxide, yellow iron sesquioxide, black iron oxide, Food Red No. 102, Food Yellow No. 4, and Food Yellow No. 5; surfactants such as sodium lauryl sulfate, sodium dioctyl sulfosuccinate, polysorbate, and polyoxyethylene hydrogenated castor oil; coating agents such as hydroxypropylmethylcellulose, aminoalkyl methacrylate copolymer E, aminoalkyl methacrylate copolymer RS, ethylcellulose, cellulose acetate phthalate, hydroxymethylcellulose phthalate, methacrylic acid copolymer L, methacrylic acid copolymer LD, and methacrylic acid copolymer S; plasticizers such as triethyl citrate, Macrogol, triacetin, and propylene glycol; pH adjusters and buffers such as sodium citrate, sodium acetate, and sodium phosphate; stabilizers such as sodium pyrosulfite, ethylenediaminetetraacetic acid, thioglycolic acid, and thiolactic acid; tonicity agents such as sodium chloride, glucose, mannitol, and glycerin; solubilizers such as sodium carboxymethylcellulose, propylene glycol, sodium benzoate, benzyl benzoate, urethane, ethanolamine, and glycerin; soothing agents such as calcium gluconate, chlorobutanol, glucose, and benzyl alcohol; and pharmaceutical additives for liquid formulations such as local anesthetics.

These additives may be used alone or in combination. The additives can be contained in any amount so that they sufficiently exhibit their effects according to their respective purposes.

The pharmaceutical composition, the medicament, or the preparation of the present invention can be administered orally or parenterally in forms such as tablets, capsules, powders, syrups, granules, pills, suspensions, emulsions, solutions, dusts, suppositories, eye drops, nasal drops, ear drops, patches, ointments, or injections according to a routine method.

Furthermore, iguratimod or a salt thereof and an immunosuppressive agent are separately formulated as active ingredients, and these preparations may be integrated into a kit and administered simultaneously or separately at time intervals either through the same route or through different routes.

An administration method, a dose, and the number of doses can be selected appropriately according to the age, body weight, and symptoms of a patient. Typically, 0.01 to 1000 mg/kg/day of each active ingredient can be administered at one or divided doses or in one portion of a few days' doses through an oral or parenteral (e.g., injection, intravenous drip, or administration to a rectal site) route to an adult.

The pharmaceutical composition, the medicament, or the preparation of the present invention can be administered through any route, for example, intravenously, orally, intramuscularly, subcutaneously, by inhalation, percutaneously, or through any of other routes and, preferably, is orally administered.

Preferably, the iguratimod or the salt thereof is administered simultaneously or separately with the immunosuppressive agent. Its administration route is preferably oral administration.

In the pharmaceutical composition, the medicament, the kit, or the method of the present invention, the ratio between the iguratimod or the salt thereof and the immunosuppressive agent in combination is usually in the range of 1:1/100 to 1:10, preferably 1:1/50 to 1:1, more preferably 1:1/10 to 1:1, by weight for both of the single preparation and respective preparations of the active ingredients.

For example, the effective amount of the iguratimod or the salt thereof administered to an adult is preferably 10 to 200 mg/day, preferably 25 to 100 mg/day (in terms of iguratimod), which can be administered at one or divided doses.

For example, the effective amount of methotrexate administered to an adult is 0.5 to 60 mg/day, preferably 0.5 to 16 mg/day, more preferably 2 to 16 mg/day, which can be administered at one or divided doses. Alternatively, the effective amount is 6 to 300 mg/week, preferably 6 to 30 mg/week, which can be administered at one or divided doses.

For example, the effective amount of prednisolone administered to an adult is 0.5 to 120 mg/day, preferably 5 to 60 mg/day, which can be administered at one or divided doses.

EXAMPLES

Next, the present invention will be described with reference to test examples. However, these examples are not intended to limit the scope of the present invention.

Iguratimod was used as a test substance. Methotrexate and prednisolone were used as immunosuppressive agents.

Test Example 1

Effect of Combined Use of Iguratimod and Methotrexate on Adjuvant-Induced Arthritis in Rats Iguratimod and methotrexate were selected as test substances.

A suspension of dead Mycobacterium tuberculosis in liquid paraffin (0.6 mg/0.1 mL) was intradermally injected in the plantar region of left hind paw of each Lewis male rat to induce adjuvant arthritis. The paw volumes of both hind legs were measured using a plethysmometer on a daily basis from before to after the induction of arthritis. The test substances were separately suspended or dissolved in 0.5% aqueous methylcellulose solutions to prepare dosing solutions, which were orally administered once a day for 21 days from immediately after the adjuvant injection. In the case of combined administration, both test substances were simultaneously administered.

The dose of iguratimod was set to 3 mg/kg, while the dose of methotrexate was set to 0.1 mg/kg. Alternatively, 3 mg/kg iguratimod and 0.1 mg/kg methotrexate were administered in combination.

1 mL of 0.5% aqueous methylcellulose solution per 100 g of body weight was orally administered to an untreated normal group and a control group that received no test substance after the induction of arthritis.

On the day after the final administration (on the 21st day after the induction of arthritis), the paw volume of the left hind leg was measured for each group. Subsequently, peripheral blood was collected therefrom, and the reticulocyte count was measured.

The swelling rate and the inhibition rate were determined according to the following formulas:

Swelling rate (%)=[(Paw volume of the left hind leg on the 21st day after arthritis induction/Paw volume of the left hind leg before arthritis induction)−1]×100

Inhibition rate (%)=100−(Swelling rate in the test substance administration group/Swelling rate in the control group)×100

The results are shown in Table 1.

TABLE 1

| Test group | Swelling rate (%) | Inhibition rate (%) |
| --- | --- | --- |
| Normal | 8 | — |
| Control | 155 | — |
| Iguratimod (3 mg/kg) | 93 | 40 |
| Methotrexate (0.1 mg/kg) | 114 | 26 |
| Iguratimod (3 mg/kg) + Methotrexate (0.1 mg/kg) | 42 | 73 |

The inhibition rate was 40% for the 3 mg/kg iguratimod administration group and 26% for the 0.1 mg/kg methotrexate administration group. By contrast, the inhibition rate was 73% for the 3 mg/kg iguratimod-0.1 mg/kg methotrexate combined administration group. As is evident, the combined use of 3 mg/kg iguratimod and 0.1 mg/kg methotrexate strongly inhibited arthritis.

The average value of reticulocyte counts in the peripheral blood of each group was determined, and its ratio (%) to the average value thereof in the normal group was determined. The results are shown in Table 2.

TABLE 2

| Test group | Reticulocyte count (%) |
| --- | --- |
| Normal | 100 |
| Control | 190 |
| Iguratimod (3 mg/kg) | 161 |
| Methotrexate (0.1 mg/kg) | 57 |
| Iguratimod (3 mg/kg) + Methotrexate (0.1 mg/kg) | 106 |

The reticulocyte count ratio was 190% for the arthritis-affected rats (control). A rise in reticulocyte count was observed, which was probably caused by increased hematopoiesis attributed to hemorrhagic lesions associated with arthritis. The reticulocyte count ratio was 57% for the 0.1 mg/kg methotrexate administration group. Hematopoiesis was inhibited to decrease the reticulocyte count to below the level of the normal group. The reticulocyte count ratio was 106% for the 3 mg/kg iguratimod-0.1 mg/kg methotrexate combined administration group. The reticulocyte count decreased by methotrexate recovered to substantially the same level as in the normal group.

Test Example 2

Effect of Combined Use of Iguratimod and Prednisolone on Adjuvant-Induced Arthritis in Rats Iguratimod and prednisolone were selected as test substances.

A suspension of dead Mycobacterium tuberculosis in liquid paraffin (0.6 mg/0.1 mL) was intradermally injected to the base of tail of each Lewis male rat to induce adjuvant arthritis. On the 18th day after the induction of arthritis, the paw volumes of both hind legs were measured. The rats were grouped so that the paw volumes of both hind legs averaged out per group. The test substances were separately suspended or dissolved in 0.5% aqueous methylcellulose solutions to prepare dosing solutions, which were orally administered once a day for 7 days from the grouping date. In the case of combined administration, both test substances were simultaneously administered through an oral route.

The dose of iguratimod was set to 1 mg/kg, while the dose of prednisolone was set to 5 mg/kg. Alternatively, 1 mg/kg iguratimod and 5 mg/kg prednisolone were orally administered in combination.

1 mL of 0.5% aqueous methylcellulose solution per 100 g of body weight was orally administered to a control group that received no test substance after the grouping.

On the day after the final administration (on the 25th day after the induction of arthritis), the paw volumes of both hind legs were measured for each group. Subsequently, the rats were killed by blood removal. Then, their thymus glands, spleens, and adrenal glands were extirpated, and the weights were measured to calculate the ratio of each organ weight to 100 g body weight.

The average swelling rate of both hind legs and the inhibition rate were determined according to the following formulas:

Swelling rate (%)=[(Paw volume on the 25th day after arthritis induction/Paw volume before arthritis induction)−1]×100

Inhibition rate (%)=100−(Swelling rate in the test substance administration group/Swelling rate in the control group)×100

The results are shown in Table 3.

TABLE 3

| Test group | Swelling rate (%) | Inhibition rate (%) |
| --- | --- | --- |
| Control | 105 | — |
| Iguratimod (1 mg/kg) | 76 | 28 |
| Prednisolone (5 mg/kg) | 66 | 37 |
| Iguratimod (1 mg/kg) + Prednisolone (5 mg/kg) | 56 | 47 |

The inhibition rate was 28% for the 1 mg/kg iguratimod administration group and 37% for the 5 mg/kg prednisolone administration group.

By contrast, the inhibition rate was 47% for the 1 mg/kg iguratimod-5 mg/kg prednisolone combined administration group. The combined use of iguratimod and prednisolone exhibited strong anti-arthritic effects.

The respective ratios of thymus gland, spleen and adrenal gland weights to the body weight were determined for each group and indicated by their ratios (%) to those in the control group. The results are shown in Table 4.

TABLE 4

| Test group | Ratio to control group (%) | | |
|---|---|---|---|
| | Thymus gland | Spleen | Adrenal gland |
| Control | 100 | 100 | 100 |
| Iguratimod (1 mg/kg) | 109 | 110 | 93 |
| Prednisolone (5 mg/kg) | 59 | 68 | 75 |
| Iguratimod (1 mg/kg) + Prednisolone (5 mg/kg) | 66 | 87 | 89 |

The weights of the thymus glands and the spleens, which are immune tissues or organs, were decreased to 59% and 68%, respectively, in the 5 mg/kg prednisolone administration group compared with the control group. Involution was observed.

By contrast, no reduction in the weights of the thymus glands and the spleens was observed in the 1 mg/kg iguratimod administration group.

Adrenal atrophy known as the physiological effect of steroidal anti-inflammatory drugs was also observed in the 5 mg/kg prednisolone administration group.

The combined administration of iguratimod and prednisolone provided a recovery from the reduction in the weights of the thymus glands, the spleens, and the adrenal glands caused by prednisolone.

As is evident from these results, the combined administration of iguratimod or a salt thereof and one or more immunosuppressive agents can potentiate anti-arthritic effects and further improve bone-marrow toxicity or a weight loss of lymphoid organs. Thus, this approach is useful in the treatment such as therapy or prevention of arthritis.

Test Example 3

Effect of Combined Use of Iguratimod and Methotrexate on Cellular Damage of HepG2 Cells, a Human Hepatocyte Line Iguratimod and methotrexate were selected as test substances.

HepG2 cells floating in a Dulbecco's modified Eagle's medium (DMEM) containing 10% fetal bovine serum (FBS) were inoculated at a concentration of $3.5 \times 10^4$ cells/0.1 mL/well to a 96-well plate and cultured at 37° C. for approximately 24 hours in a 5% $CO_2$ atmosphere. Then, the medium was replaced by DMEM containing iguratimod and methotrexate and containing 0.5% FBS, and the cells were further cultured therein for 24 hours. In this context, iguratimod was dissolved in a 1.12-fold molar quantity of 0.1 mol/L sodium hydroxide solution, diluted with distilled water, and then added to the culture solution. Methotrexate was dissolved in dimethyl sulfoxide (DMSO) and added to the culture solution. Test substance-free DMEM containing 0.25% DMSO and 0.5% FBS was used in a control group.

After the completion of culture, each culture supernatant was separated, and the activity of lactate dehydrogenase (LDH) released outside the cells was determined using Cytotoxicity Detection Kit (LDH) (Roche Applied Science). In order to determine LDH activity in the whole cells, 0.1 mL of DMEM containing 2% Triton X-100 and 0.5% FBS was then added to each well after the culture supernatant separation to prepare a cell lysate. The LDH activity was determined in the same way as above.

The rate of LDH release (%) was calculated according to the formula shown below and indicated by the average value of each group. Its ratio with respect to the control group was also determined.

Rate of LDH release (%)=Activity in the culture supernatant/(Activity in the culture supernatant+ Activity in the cell lysate)×100

The results are shown in Table 5.

TABLE 5

| Test group | Iguratimod concentration (μg/mL) | Methotrexate concentration (μg/mL) | Rate of LDH release (%) | Ratio to control group (%) |
|---|---|---|---|---|
| Control | 0 | 0 | 14.2 | — |
| Iguratimod | 3 | 0 | 15.9 | 112 |
| | 30 | 0 | 17.0 | 120 |
| Methotrexate | 0 | 1 | 24.4 | 172 |
| | 0 | 10 | 26.8 | 189 |
| Iguratimod + methotrexate | 3 | 1 | 22.3 | 158 |
| | 3 | 10 | 20.0 | 141 |

The addition of 3 or 30 μg/mL iguratimod only slightly increased the rate of LDH release in the lysate of the human hepatocyte line HepG2 cells, whereas the addition of 1 or 10 methotrexate increased the rate of LDH release by 70% to nearly 90%. This result reflects hepatocellular damage brought about by methotrexate. By contrast, the combined use of iguratimod and methotrexate evidently decreased the rate of LDH release.

As is evident from these results, iguratimod or a salt thereof can reduce hepatocellular damage brought about by an immunosuppressive agent. The combined administration thereof is also useful in the treatment of arthritis from viewpoints other than efficacy. Even for patients that are difficult to treat due to an adverse reaction attributed to an immunosuppressive agent, the administration of iguratimod can reduce the adverse reaction attributed to the immunosuppressive agent and thus allows the therapy to be continued. Also, iguratimod or a salt thereof can be used for reducing such an adverse reaction.

Next, the present invention will be described with reference to Examples. However, the present invention is not intended to be limited to them.

Example 1

2.5 g of iguratimod (Toyama Chemical Co., Ltd.), 15.9 g of crystalline cellulose (Asahi Kasei Chemicals Corp; CEOLUS PH-101), 0.7 g of carmellose calcium (Gotoku Chemical Co., Ltd.; ECG-505), and 0.2 g of hydroxypropylcellulose (Nippon Soda Co., Ltd.; HPC-L) were mixed using a mortar. Water was added thereto, and the mixture was kneaded. The kneaded product was sifted through a 20-mesh sieve, dried overnight at 40° C., and then sifted through a 16-mesh sieve to obtain a granulated powder. The obtained granulated powder was supplemented and mixed with 0.7 g of carmellose calcium and 0.04 g of magnesium stearate (Merck; Magnesium Stearate) to obtain a powder for tableting. The obtained powder for tableting was compressed using a pestle of 8.0 mm in diameter in a rotary tableting machine to obtain round tablets each containing 25 mg of iguratimod per tablet (200 mg).

Example 2

2.5 g of iguratimod (Toyama Chemical Co., Ltd.), 15.9 g of crystalline cellulose (Asahi Kasei Chemicals Corp; CEOLUS PH-101), 1.4 g of croscarmellose sodium (Asahi Kasei Chemicals Corp; KICCOLATE ND-200), and 0.2 g of hydroxypropylcellulose (Nippon Soda Co., Ltd.; HPC-L) were mixed using a mortar. Water was added thereto, and the mixture was kneaded. The kneaded product was sifted through a 20-mesh sieve, dried overnight at 40° C., and then sifted through a 16-mesh sieve to obtain a granulated powder. The obtained granulated powder was supplemented and mixed with 0.04 g of magnesium stearate (Merck; Magnesium Stearate) to obtain a powder for tableting. The obtained powder for tableting was compressed using a pestle of 8.0 mm in diameter in a rotary tableting machine to obtain round tablets each containing 25 mg of iguratimod per tablet (200 mg).

Example 3

2.5 g of iguratimod (Toyama Chemical Co., Ltd.), 15.9 g of crystalline cellulose (Asahi Kasei Chemicals Corp; CEOLUS PH-101), 1.4 g of low-substituted hydroxypropylcellulose (Shin-Etsu Chemical Co., Ltd.; L-HPC), and 0.2 g of hydroxypropylcellulose (Nippon Soda Co., Ltd.; HPC-L) were mixed using a mortar. Water was added thereto, and the mixture was kneaded. The kneaded product was sifted through a 20-mesh sieve, dried overnight at 40° C., and then sifted through a 16-mesh sieve to obtain a granulated powder. The obtained granulated powder was supplemented and mixed with 0.04 g of magnesium stearate (Merck; Magnesium Stearate) to obtain a powder for tableting. The obtained powder for tableting was compressed using a pestle of 8.0 mm in diameter in a rotary tableting machine to obtain round tablets each containing 25 mg of iguratimod per tablet (200 mg).

Example 4

2.5 g of iguratimod (Toyama Chemical Co., Ltd.), 2.5 g of crystalline cellulose (Asahi Kasei Chemicals Corp; CEOLUS PH-101), and 0.5 g of light anhydrous silicic acid (Freund Corp.; Adsolider 101) were mixed and pulverized using a mortar. This powder was supplemented and mixed with 16.5 g of D-mannitol (Towa-Kasei Co., Ltd.; Mannit P), 2.5 g of carmellose (Gotoku Chemical Co., Ltd.; NS-300), and 0.25 g of hydroxypropylcellulose (Nippon Soda Co., Ltd.; HPC-L). Water was added to the mixture, and the resulting mixture was kneaded. The kneaded product was sifted through a 20-mesh sieve, dried overnight at 40° C., and then sifted through a 16-mesh sieve to obtain a granulated powder. The obtained granulated powder was supplemented and mixed with 0.25 g of magnesium stearate (Merck; Magnesium Stearate) to obtain a powder for tableting. The obtained powder for tableting was compressed using a pestle of 8.5 mm in diameter in a rotary tableting machine to obtain round tablets each containing 25 mg of iguratimod per tablet (250 mg).

Example 5

2.5 g of iguratimod (Toyama Chemical Co., Ltd.), 2.5 g of crystalline cellulose (Asahi Kasei Chemicals Corp; CEOLUS PH-101), and 0.5 g of light anhydrous silicic acid (Freund Corp.; Adsolider 101) were mixed and pulverized using a mortar. This powder was supplemented and mixed with 0.2 g of methotrexate (Japanese Pharmacopoeia). This mixture was further supplemented and mixed with 5 g of corn starch (Nihon Shokuhin Kako Co., Ltd.; Nisshoku Corn Starch W), 11.4 g of lactose hydrate (DMV; Pharmatose 200M), 2.5 g of low-substituted hydroxypropylcellulose (Shin-Etsu Chemical Co., Ltd.; L-HPC), and 0.25 g of hydroxypropylcellulose (Nippon Soda Co., Ltd.; HPC-L). Water was added to the mixture, and the resulting mixture was kneaded. The kneaded product was sifted through a 20-mesh sieve, dried overnight at 40° C., and then sifted through a 16-mesh sieve to obtain a granulated powder. The obtained granulated powder was supplemented and mixed with 0.15 g of magnesium stearate (Merck; Magnesium Stearate) to obtain a powder for tableting. The obtained powder for tableting was compressed using a pestle of 8.5 mm in diameter in a rotary tableting machine to obtain round tablets each containing 25 mg of iguratimod and 2 mg of methotrexate per tablet (250 mg).

Example 6

2.5 g of iguratimod (Toyama Chemical Co., Ltd.), 2.65 g of crystalline cellulose (Asahi Kasei Chemicals Corp; CEOLUS PH-101), and 0.5 g of light anhydrous silicic acid (Freund Corp.; Adsolider 101) were mixed and pulverized using a mortar. This powder was supplemented and mixed with 0.05 g of methotrexate (Japanese Pharmacopoeia). This mixture was further supplemented and mixed with 5 g of corn starch (Nihon Shokuhin Kako Co., Ltd.; Nisshoku Corn Starch W), 11.4 g of lactose hydrate (DMV; Pharmatose 200M), 2.5 g of low-substituted hydroxypropylcellulose (Shin-Etsu Chemical Co., Ltd.; L-HPC), and 0.25 g of hydroxypropylcellulose (Nippon Soda Co., Ltd.; HPC-L). Water was added to the mixture, and the resulting mixture was kneaded. The kneaded product was sifted through a 20-mesh sieve, dried overnight at 40° C., and then sifted through a 16-mesh sieve to obtain a granulated powder. The obtained granulated powder was supplemented and mixed with 0.15 g of magnesium stearate (Merck; Magnesium Stearate) to obtain a powder for tableting. The obtained powder for tableting was compressed using a pestle of 8.5 mm in diameter in a rotary tableting machine to obtain round tablets each containing 25 mg of iguratimod and 0.5 mg of methotrexate per tablet (250 mg).

Example 7

2.5 g of iguratimod (Toyama Chemical Co., Ltd.), 2.6 g of crystalline cellulose (Asahi Kasei Chemicals Corp; CEOLUS PH-101), and 0.5 g of light anhydrous silicic acid (Freund Corp.; Adsolider 101) were mixed and pulverized using a mortar. This powder was supplemented and mixed with 0.1 g of methotrexate (Japanese Pharmacopoeia). This mixture was further supplemented and mixed with 5 g of corn starch (Nihon Shokuhin Kako Co., Ltd.; Nisshoku Corn Starch W), 11.4 g of lactose hydrate (DMV; Pharmatose 200M), 2.5 g of low-substituted hydroxypropylcellulose (Shin-Etsu Chemical Co., Ltd.; L-HPC), and 0.25 g of hydroxypropylcellulose (Nippon Soda Co., Ltd.; HPC-L). Water was added to the mixture, and the resulting mixture was kneaded. The kneaded product was sifted through a 20-mesh sieve, dried overnight at 40° C., and then sifted through a 16-mesh sieve to obtain a granulated powder. The obtained granulated powder was supplemented and mixed with 0.15 g of magnesium stearate (Merck; Magnesium Stearate) to obtain a powder for tableting. The obtained powder for tableting was compressed using a pestle of 8.5 mm in diameter in a rotary tableting machine to obtain round tablets each containing 25 mg of iguratimod and 1 mg of methotrexate per tablet (250 mg).

Example 8

0.2 g of methotrexate (Japanese Pharmacopoeia), 1.5 g of corn starch (Nihon Shokuhin Kako Co., Ltd.; Nisshoku Corn Starch W), and 3.5 g of lactose hydrate (DMV; Pharmatose 200M) were mixed using a mortar. This mixture was supplemented and mixed with 5.1 g of corn starch, 11.8 g of lactose hydrate, 2.5 g of low-substituted hydroxypropylcellulose (Shin-Etsu Chemical Co., Ltd.; L-HPC), and 0.25 g of hydroxypropylcellulose (Nippon Soda Co., Ltd.; HPC-L). Water was added to the mixture, and the resulting mixture was kneaded. The kneaded product was sifted through a 20-mesh sieve, dried overnight at 40° C., and then sifted through a 16-mesh sieve to obtain a granulated powder. The obtained granulated powder was supplemented and mixed with 0.15 g of magnesium stearate (Merck; Magnesium Stearate) to obtain a powder for tableting. The obtained powder for tableting was compressed using a pestle of 8.5 mm in diameter in a rotary tableting machine to obtain round tablets each containing 2 mg of methotrexate per tablet (250 mg).

Example 9

0.2 g of prednisolone (Japanese Pharmacopoeia), 1.5 g of corn starch (Nihon Shokuhin Kako Co., Ltd.; Nisshoku Corn Starch W), and 3.5 g of lactose hydrate (DMV; Pharmatose 200M) were mixed using a mortar. This mixture was supplemented and further mixed with 3.2 g of corn starch, 7.5 g of lactose hydrate, 0.9 g of carmellose calcium (Gotoku Chemical Co., Ltd.; ECG-505), and 0.2 g of hydroxypropylcellulose (Nippon Soda Co., Ltd.; HPC-L). Water was added to the mixture, and the resulting mixture was kneaded. The kneaded product was sifted through a 20-mesh sieve, dried overnight at 40° C., and then sifted through a 16-mesh sieve to obtain a granulated powder. The obtained granulated powder was supplemented and mixed with 0.9 g of carmellose calcium and 0.1 g of magnesium stearate (Merck; Magnesium Stearate) to obtain a powder for tableting. The obtained powder for tableting was compressed using a pestle of 6.5 mm in diameter in a rotary tableting machine to obtain round tablets each containing 1 mg of prednisolone per tablet (90 mg).

Example 10

0.5 g of prednisolone (Japanese Pharmacopoeia), 1.5 g of corn starch (Nihon Shokuhin Kako Co., Ltd.; Nisshoku Corn Starch W), and 3.5 g of lactose hydrate (DMV; Pharmatose 200M) were mixed using a mortar. This mixture was supplemented and further mixed with 2.3 g of corn starch, 5.47 g of lactose hydrate, 0.75 g of carmellose calcium (Gotoku Chemical Co., Ltd.; ECG-505), and 0.15 g of hydroxypropylcellulose (Nippon Soda Co., Ltd.; HPC-L). Water was added to the mixture, and the resulting mixture was kneaded. The kneaded product was sifted through a 20-mesh sieve, dried overnight at 40° C., and then sifted through a 16-mesh sieve to obtain a granulated powder. The obtained granulated powder was supplemented and mixed with 0.75 g of carmellose calcium and 0.08 g of magnesium stearate (Merck; Magnesium Stearate) to obtain a powder for tableting. The obtained powder for tableting was compressed using a pestle of 7.5 mm in diameter in a rotary tableting machine to obtain round tablets each containing 5 mg of prednisolone per tablet (150 mg).

Example 11

2.5 g of iguratimod (Toyama Chemical Co., Ltd.), 2.5 g of crystalline cellulose (Asahi Kasei Chemicals Corp; CEOLUS PH-101), and 0.5 g of light anhydrous silicic acid (Freund Corp.; Adsolider 101) were mixed and pulverized using a mortar. This powder was supplemented and mixed with 1 g of prednisolone (Japanese Pharmacopoeia). This mixture was further supplemented and mixed with 4.6 g of corn starch (Nihon Shokuhin Kako Co., Ltd.; Nisshoku Corn Starch W), 11 g of lactose hydrate (DMV; Pharmatose 200M), 1.25 g of carmellose calcium (Gotoku Chemical Co., Ltd.; ECG-505), and 0.25 g of hydroxypropylcellulose (Nippon Soda Co., Ltd.; HPC-L). Water was added to the mixture, and the resulting mixture was kneaded. The kneaded product was sifted through a 20-mesh sieve, dried overnight at 40° C., and then sifted through a 16-mesh sieve to obtain a granulated powder. The obtained granulated powder was supplemented and mixed with 1.25 g of carmellose calcium and 0.15 g of magnesium stearate (Merck; Magnesium Stearate) to obtain a powder for tableting. The obtained powder for tableting was compressed using a pestle of 8.5 mm in diameter in a rotary tableting machine to obtain round tablets each containing 25 mg of iguratimod and 10 mg of prednisolone per tablet (250 mg).

The method using iguratimod or a salt thereof and one or more immunosuppressive agents in combination is useful as a method for treating autoimmune diseases with a reduced adverse reaction. A pharmaceutical composition containing these ingredients is useful in the treatment of autoimmune diseases.

The method and the pharmaceutical composition of the present invention are useful in the treatment of more severe autoimmune diseases.

The invention claimed is:
1. A method of reducing methotrexate-induced hepatocellular damage in a subject having arthritis, wherein said method comprises,
    administering an amount of methotrexate to the subject in an amount and frequency that is therapeutically effective to treat the subject's arthritis and induce hepatocellular damage, and
    after hepatocellular damage is induced, continuing to administer methotrexate to the subject in the same amount and frequency that induced hepatocellular damage in combination with an amount of iguratimod that reduces the methotrexate-induced hepatocellular damage, and
    wherein a ratio of methotrexate to iguratimod administered to the subject ranges from 1:1 to 10:1 by weight percentage.
2. The method of claim 1, wherein the combination of methotrexate and iguratimod administered to the subject further comprises an agent selected from the group consisting of a sugar alcohol, a sugar, a cellulose, a starch, water, ethyl alcohol, Macrogol, propylene glycol, citric acid, acetic acid, phosphoric acid, lactic acid, sodium lactate, sulfuric acid, sodium hydroxide, white petrolatum, polyethylene, paraffin, glycerin, cellulose derivatives, polyethylene glycol, silicon, bentonite, a disintegrant, a binder, a lubricant, a corrigent, a coloring agent, a surfactant, a coating agent, a plasticizer, a buffer, a tonicity agent, a solubilizer, and a soothing agent.

* * * * *